United States Patent [19]

Zeeh et al.

[11] 4,336,055
[45] Jun. 22, 1982

[54] AGENTS FOR REGULATING PLANT GROWTH CONTAINING TRIAZOLYL GLYCOL ETHERS, AND THE USE THEREOF

[75] Inventors: Bernd Zeeh; Ernst Buschmann, both of Ludwigshafen; Johann Jung, Limburgerhof, all of Fed. Rep. of Germany

[73] Assignee: BASF Aktiengesellschaft, Fed. Rep. of Germany

[21] Appl. No.: 155,749

[22] Filed: Jun. 2, 1980

[30] Foreign Application Priority Data

Jun. 26, 1979 [DE] Fed. Rep. of Germany ....... 2925687

[51] Int. Cl.$^3$ .................. A01N 43/64; C07D 249/10
[52] U.S. Cl. ............................................ 71/76; 71/92; 548/262
[58] Field of Search ...................... 71/76, 92; 548/262

[56] References Cited

U.S. PATENT DOCUMENTS

| 4,229,459 | 10/1980 | Kramer et al. | 424/269 |
| 4,233,311 | 11/1980 | Kramer et al. | 424/269 |

FOREIGN PATENT DOCUMENTS

| 2640823 | 3/1977 | Fed. Rep. of Germany | 548/262 |
| 2650831 | 5/1978 | Fed. Rep. of Germany | 548/262 |
| 2720868 | 11/1978 | Fed. Rep. of Germany | 548/262 |
| 2739352 | 3/1979 | Fed. Rep. of Germany | 548/262 |

OTHER PUBLICATIONS

Tolbert, J. Biol. Chem., vol. 235, pp. 475–479 (1960).

*Primary Examiner*—Alton D. Rollins
*Attorney, Agent, or Firm*—Keil & Witherspoon

[57] ABSTRACT

Agents for regulating plant growth containing a triazolyl glycol ether of the formula

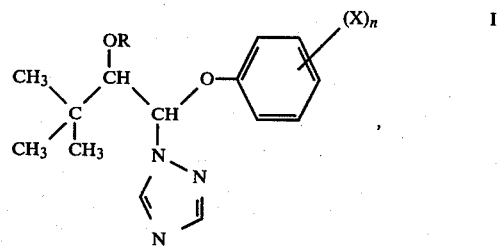

where R denotes alkyl, cycloalkyl, alkenyl or alkynyl which are unsubstituted or substituted by from 1 to 3 halogen atoms, X denotes hydrogen, halogen or phenyl, and n denotes one of the integers 1, 2 and 3, or a salt thereof, a process for the manufacture of such agents, and their use.

2 Claims, No Drawings

AGENTS FOR REGULATING PLANT GROWTH CONTAINING TRIAZOLYL GLYCOL ETHERS, AND THE USE THEREOF

The present invention relates to agents for regulating plant growth containing triazolyl glycol ethers.

It has been disclosed that 2-chloroethyltrimethylammonium chloride (CCC) has growth-regulating properties in cereals and other crop plants (J. Biol. Chem., 235, 475, 1960). However, when agents containing this compound are used to regulate plant growth, the action, particularly at low application rates and concentrations, is often not satisfactory.

It has further been disclosed to use triazolyl allyl ethers for regulating plant growth (German Laid-Open Application DE-OS No. 2,650,831). Furthermore, the suitability of phenyl butyl ketones substituted by triazole for regulating plant growth has been disclosed (German Laid-Open Application DE-OS No. 2,739,352).

We have now found that triazolyl glycol ethers of the formula

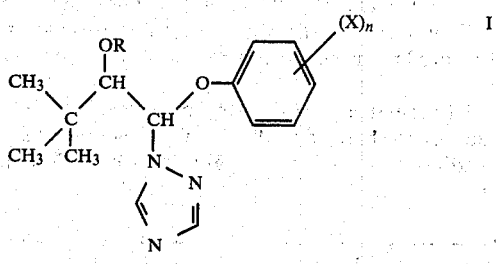

where R denotes alkyl (e.g., methyl, ethyl, propyl, butyl), cycloalkyl, alkenyl (e.g., allyl, crotyl, 3-methyl-2-buten-1-yl) or alkynyl (e.g., propargyl), R being unsubstituted or substituted by from 1 to 3 halogen atoms, X denotes hydrogen, alkyl (e.g., methyl, ethyl, tert-butyl) or halogen (fluorine, chlorine, bromine, iodine) and n denotes one of the integers 1, 2 and 3, and the salts of these compounds, particularly salts tolerated by crop plants (e.g., hydrochlorides, hydrobromides, sulfates, nitrates, oxalates, acetates), have an excellent growth-regulating action.

Examples of meanings for R are methyl, ethyl, propyl, isopropyl, n-butyl, isobutyl, 1-methylpropyl, n-pentyl, 1-methylpentyl, 2-methylpentyl, 3-methylpentyl, 4-methylpentyl, allyl, crotyl, methallyl, propargyl, butyn-2-yl, 2,3-dichloroallyl, 2,3,3-trichlorallyl, cyclohexyl and cyclopentyl.

Examples of meanings for X are hydrogen, chlorine, fluorine, bromine and iodine.

The active ingredients influence plant metabolism and are therefore suitable as growth regulators.

Plant growth regulators may have several different effects on plants. The action of the compounds depends essentially on the time applied, with reference to the development stage of the seed or plant, on the amount of active ingredient applied to the plants or their habitat, and on the application method employed. At all events, growth regulators are intended to influence crop plants in a desired manner.

Plant growth-regulating compounds may be used for instance to inhibit vegetative plant growth. It is important to inhibit the growth of herbaceous and woody plants on roadsides and in the vicinity of overhead transmission lines, or quite generally where vigorous growth is undesired.

A further important application area for growth regulators is the inhibition of upward plant growth for instance in soybeans; a reduction in stem length reduces or completely eliminates the danger of lodging before the plants are harvested.

The inhibition of vegetative growth also makes closer planting possible in numerous crops, which means an increase in yield based on the area cropped.

A further mechanism for increasing yields with plant growth regulators is based on the fact that blossom and fruit formation benefits to a greater extent from the nutrients when vegetative growth is restricted.

However, plant growth regulators may also frequently be employed to promote vegetative growth. This is of great use when the vegetative plant parts are harvested. The promotion of vegetative growth may, however, simultaneously result in an increase in generative growth, e.g., the formation of more or bigger fruit.

Increases in yield may also be achieved in many instances by influencing plant metabolism without there being any noticeable change in vegetative growth. Growth regulators may also change the composition of plants and thus improve the quality of the harvested products. It is for example possible to increase the sugar content of sugar beets, sugarcane, pineapples and citruses, or to raise the protein content in soybeans and cereals.

Parthenocarpic fruits may also be formed under the influence of growth regulators. Further, the sex of the flowers may be influenced.

The production or the flow of secondary plant materials may also be positively influenced with growth regulators. The stimulation of latex flow in rubber trees may be mentioned by way of example.

During the growth of the plant, branching may be increased by growth regulators as a result of the chemical control of apical dominance. This is of interest for instance in the propagation of plant cuttings. It is, however, also possible to inhibit the growth of lateral branches, e.g., to prevent sucker growth in tobacco plants after topping, and thus to promote leaf growth.

Growth regulators may also be used to defoliate plants at any desired time. Such a defoliation facilitates mechanical harvesting, e.g., in grapes or cotton, or reduces transpiration at a time when the plant is to be transplanted.

Premature fruit drop may also be prevented by growth regulators. It is, however, also possible to thin out chemically by promoting fruit drop to a certain extent. Growth regulators may also be used to reduce the force to be exerted for plucking off fruit from crop plants at harvest time, making mechanical harvesting possible, or facilitating manual harvesting.

Further, growth regulators may be used to accelerate or delay the ripening of material before or after harvesting. This feature is of particular advantage, because market needs can be optimally accommodated. Growth regulators may also in many cases improve fruit color. It is also possible to concentrate ripening with growth regulators, thus making it possible, for example in tobacco, tomatoes or coffee, to harvest completely mechanically or manually in just one operation.

Growth regulators can also influence the dormancy of seeds or buds, i.e., the annual endogenous rhythm; plants such as pineapples or ornamentals in nurseries can thus be made to germinate, sprout or blossom at a time at which they normally show no willingness to do so.

Growth regulators may further be employed to delay budding or seed germination, for example in order in frostendangered areas to prevent damage by late frosts.

Growth regulators may also make crop plants halophilic, i.e., they may be cultivated in salty soils.

Growth regulators can also make plants more frost- and drought-resistant.

Some of the active ingredients are disclosed in German Laid-Open Application DE-OS No. 2,720,949. They are obtained for instance by reacting triazolyl glycols (disclosed in German Laid-Open Application DE-OS No. 2,324,010) of the formula

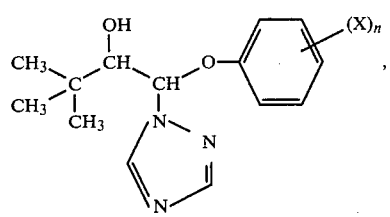
II where X and n have the above meanings, in the presence of bases and in solvents, with alkylating agents of the formula

R—X    III, where R has the above meanings and X denotes an eliminable group, e.g., halogen,

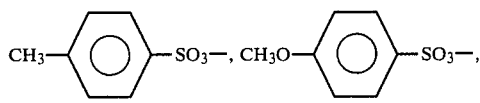

or $OSO_3R$. The phase transfer method (E. V. Dehmlow, Angew. Chem., 89, 521–533, 1977) is also well suited for this reaction.

The following directions illustrate the manufacture of the compounds of the formula I.

50 g of 50% (wt%) strength aqueous NaOH is dripped into a solution of 14.8 g of 1-(4-chlorophenoxy)-1-(1,2,4-triazol-1-yl)-3,3-dimethylbutan-2-ol and 9 g of tetrabutylammonium bisulfate in 100 ml of 1,2,3-trichloropropene. The temperature is kept below 30° C. by ice cooling. After the mixture has been stirred for 24 hours at room temperature (20° C.), 150 ml of ether and 50 ml of water are added. The organic phase is washed three times with 50 ml of water, dried with $Na_2SO_4$ and concentrated. The oily crude product is taken up in $CH_2Cl_2$ and chromatographed on silica gel. There is obtained 7.2 g of a colorless oil. The product has the following structural formula

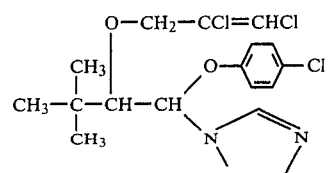

Elemental analysis:

|  | C | H | O | N | Cl |
|---|---|---|---|---|---|
| calc.: | 50.5 | 5.0 | 7.9 | 10.4 | 26.3 |
| found: | 50.5 | 5.0 |  | 10.1 | 26.3 |

The nmr spectrum ($CDCl_3$, δ values) reveals 2 diastereoisomers:

Isomer 1: 0.90 (s, 9H), 3.78 (d, J=3 Hz, 1H), 4.62 (d, J=12 Hz, 1H), 5.83 (d, J=12 Hz, 1H), 6.42 (d, J=3 Hz, 1H), 6.43 (s, 1H), 6.82 (d, J=9 Hz, 2H), 7.21 (d, J=9 Hz, 2H), 7.96 (s, 1H), 8.63 (s, 1H)

Isomer 2: 0.90 (s, 9H), 3.74 (d, J=3 Hz, 1H), 4.38 (d, J=12 Hz, 1H), 4.52 (d, J=12 Hz, 1H), 6.37 (d, J=3 Hz, 1H), 6.41 (s, 1H), 6.82 (d, J=9 Hz, 2H), 7.21 (d, J=9 Hz, 2H), 7.97 (s, 1H), 8.56 (s, 1H)

Examples of other active ingredients which may be prepared in the above manner are given in the following table.

Elemental analysis of the compounds listed in the table corresponded with the values calculated for them. Additional identification was provided by $^1H$-nmr spectra.

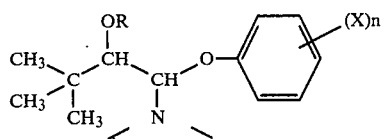

| No. | R | (X)n | M.p. °C. |
|---|---|---|---|
| 1 | $CH_3$ | 4-Cl | oil |
| 2 | $C_2H_5$ | 4-Cl | oil |
| 3 | n-$C_3H_7$ | 4-Cl | oil |
| 4 | n-$C_4H_9$ | 4-Cl | 60-62 |
| 5 | $CH_2$—$CH(CH_3)_2$ | 4-Cl | oil |
| 6 | n-$C_5H_{11}$ | 4-Cl |  |
| 7 | $CH_2CHCH_3CH_2CH_2CH_3$ | 4-Cl |  |
| 8 | $CH_2CH_2CH(CH_3)_2$ | 4-Cl |  |
| 9 | $CH_2$—CH=$CH_2$ | 4-Cl |  |
| 10 | $CH_2$—CH=CH—$CH_3$ | 4-Cl | oil |
| 11 | $CH_2CCH_3$=$CH_2$ | 4-Cl | oil |
| 12 | $CH_2$—$CH_2CH$=$CH_2$ | 4-Cl |  |
| 13 | $CH_2CCH_3$=$CHCH_3$ | 4-Cl |  |
| 14 | $CH_2CH$=$C(CH_3)_2$ | 4-Cl |  |
| 15 | $CH_2C$≡CH | 4-Cl | oil |
| 16 | $CH_2$—C≡$CCH_3$ | 4-Cl | oil |
| 17 | $CH_2CCl$=CHCl | 4-Cl | oil |
| 18 | $CH_3$ | 2,4-Cl | 153 |
| 19 | $CH_3$ | 2-Cl | oil |
| 20 | $CH_2CH$=$CH_2$ | 2-Cl | oil |
| 21 | $CH_3$ | 4-Br | oil |
| 22 | $CH_2CH$=$CH_2$ | 4-Br | 157 |
| 23 | $CH_3$ | H |  |
| 24 | $CH_2CH$=$CH_2$ | H |  |
| 25 | $CH_2CCl$=CHCl | H |  |
| 26 | $CHCH_3CH$=$CH_2$ | 4-Cl | oil |
| 27 | $CH_3$ | 4-F |  |

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations, and the ready-to-use preparations obtained therefrom, e.g. solutions, emulsions, suspensions, powders, dusts, pastes or granules, are applied in the conventional manner, e.g., spraying, atomizing, dusting, scattering or watering, or as seed disinfectants.

The formulations in general contain from 0.5 to 95 percent by weight of active ingredient, preferably from 1 to 90 percent. Application rates are from 0.01 to 10, preferably from 0.1 to 5, kg of active ingredient per hectare.

EXAMPLE 1

90 parts by weight of compound 1 is mixed with 10 parts by weight of N-methyl-α-pyrrolidone. A mixture is obtained which is suitable for application in the form of very fine drops.

EXAMPLE 2

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 3

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 4

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 5

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 6

3 parts by weight of compound 3 is intimately mixed with 97 parts by weight of particulate kaolin. A dust is obtained containing 3% by weight of the active ingredient.

EXAMPLE 7

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 8

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 9

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

To determine the growth-regulating properties of the active ingredients, soil provided with sufficient nutrients was filled into plastic pots about 12.5 cm in diameter and test plants were grown therein.

In the preemergence treatment, the compounds to be tested were sprayed onto the seedbed as aqueous formulations on the day the seeds were sown.

In the postemergence treatment, the compounds to be tested were sprayed onto the plants as aqueous formulations. The growth-regulating action observed was confirmed at the end of the experiment by height measurements. The values obtained were compared with those for untreated plants. Three prior art compounds were used for comparison purposes.

Not only was growth height reduced—the leaves also took on a more intense color. The increased chlorophyll content is indicative of a higher rate of photosynthesis, making for bigger yields.

The individual data are given in the tables below.

Comparative agents

CCC $$CH_3-\overset{\overset{CH_3}{|}}{\underset{\underset{CH_3}{|}}{N^{\oplus}}}-CH_2-CH_2-Cl \; Cl^{\ominus}$$

A (disclosed in German Laid-Open Application DE-OS 2,650,831)

[structure: bromophenyl-CH(triazolyl)-O-CH₂-CH=CH₂ · HNO₃]

B (disclosed in German Laid-Open Application DE-OS 2,739,352)

[structure: chlorophenyl-C(=O)-CH₂-CH(triazolyl)-C(CH₃)₃]

| Active ingredient (a.i.) | mg of a.i./vessel | Growth height cm | % |
|---|---|---|---|
| Summer rape, "Cosa" Preemergence; duration of expt.: 21 days | | | |
| untreated | — | 19.8 | 100 |
| CCC | 3 | 17.5 | 88.4 |
| | 12 | 16.5 | 83.3 |
| A | 3 | 18.5 | 93.4 |
| | 12 | 13.5 | 68.2 |
| B | 3 | 18.0 | 90.2 |
| | 12 | 14.0 | 70.7 |
| 16 | 3 | 17.0 | 85.9 |
| | 12 | 12.0 | 60.6 |
| Summer rape, "Petronova" Postemergence; duration of expt.: 21 days | | | |
| untreated | — | 22.1 | 100 |
| CCC | 1.5 | 21.0 | 95.0 |
| | 6 | 21.0 | 95.0 |
| A | 1.5 | 20.0 | 90.5 |
| | 6 | 18.5 | 83.7 |
| B | 1.5 | 20.0 | 90.5 |
| | 6 | 18.0 | 81.4 |
| 1 | 1.5 | 18.5 | 83.7 |
| | 6 | 16.0 | 72.4 |
| 9 | 1.5 | 19.5 | 88.2 |
| | 6 | 15.5 | 70.1 |

| Active ingredient | mg of a.i./vessel | Growth height cm | % |
|---|---|---|---|
| Summer rape, "Cosa" Postemergence; duration of expt.: 21 days | | | |
| untreated | — | 20.3 | 100 |
| CCC | 1.5 | 18.0 | 88.7 |
| | 6 | 17.0 | 83.7 |
| B | 1.5 | 17.5 | 86.2 |
| | 6 | 16.5 | 81.3 |
| 3 | 1.5 | 17.5 | 86.2 |
| | 6 | 13.5 | 66.5 |
| 4 | 1.5 | 16.5 | 81.3 |
| | 6 | 15.0 | 73.9 |
| 10 | 1.5 | 14.0 | 69.0 |
| | 6 | 11.0 | 54.2 |
| 11 | 1.5 | 15.5 | 76.4 |
| | 6 | 12.5 | 61.6 |
| 26 | 1.5 | 15.0 | 73.9 |
| | 6 | 11.5 | 56.7 |
| Soybeans, "SRF 450" Postemergence; duration of expt.: 29 days | | | |
| untreated | — | 26.3 | 100 |
| CCC | 1.5 | 24.0 | 91.3 |
| | 6 | 22.0 | 83.7 |
| A | 1.5 | 25.0 | 95.1 |
| | 6 | 21.0 | 79.9 |
| B | 1.5 | 26.0 | 98.9 |
| | 6 | 25.5 | 97.0 |
| 1 | 1.5 | 20.0 | 76.1 |
| | 6 | 17.0 | 64.6 |
| 9 | 1.5 | 23.0 | 87.5 |
| | 6 | 20.0 | 76.1 |
| Soybeans "SRF 450" Postemergence; duration of expt.: 38 days | | | |
| untreated | — | 25.3 | 100 |
| CCC | 1.5 | 25.0 | 98.8 |
| | 6 | 22.0 | 87.0 |
| B | 1.5 | 25.0 | 98.8 |
| | 6 | 22.0 | 87.0 |
| 15 | 1.5 | 19.0 | 75.1 |
| | 6 | 16.5 | 65.2 |
| 18 | 1.5 | 22.0 | 87.0 |
| | 6 | 21.0 | 83.0 |
| 21 | 1.5 | 20.0 | 79.1 |
| | 6 | 17.5 | 69.2 |
| 22 | 1.5 | 22.5 | 88.9 |
| | 6 | 19.0 | 75.1 |
| Cotton "Delta Pine" Postemergence; duration of expt.: 27 days | | | |
| untreated | — | 27.6 | 100 |
| B | 1.5 | 27.5 | 99.6 |
| | 3 | 27.0 | 97.8 |
| 1 | 1.5 | 26.0 | 94.2 |
| | 3 | 24.0 | 87.0 |
| 9 | 1.5 | 24.0 | 87.0 |
| | 3 | 24.0 | 87.0 |
| 15 | 1.5 | 25.0 | 90.6 |
| | 3 | 20.0 | 72.5 |
| 21 | 1.5 | 25.0 | 90.6 |
| | 3 | 24.0 | 87.0 |
| 22 | 1.5 | 25.0 | 90.6 |
| | 3 | 22.5 | 81.5 |

We claim:

1. A process for reducing the growth height of plants which comprises applying to the plants or to soil containing the seeds of the plants an effective amount of a triazolyl glycol ether of the formula

[structure I: (CH₃)₃C-CH(OR)-CH(triazolyl)-O-phenyl-(X)ₙ]

wherein R is alkyl of 1 to 6 carbon atoms, cycloalkyl of 5 to 6 carbon atoms, allyl, crotyl, methallyl, propargyl, or butyn-2-yl, which alkyl, cycloalkyl, alkenyl or alkynyl groups are unsubstituted or are substituted by from 1 to 3 halogen atoms, X is hydrogen, halogen or phenyl, and n is one of the integers 1, 2 or 3, or a salt thereof.

2. A process as set forth in claim 1 wherein R is methyl, ethyl, propyl, isopropyl, n-butyl, isobutyl, 1-methylpropyl, n-pentyl, 1-methylpentyl, 2-methylpentyl, 3-methylpentyl, 4-methylpentyl, allyl, crotyl, methallyl, propargyl, butyn-2-yl, 2,3-dichloroallyl, 2,3,3-trichloroallyl, cyclohexyl or cyclopentyl.

* * * * *